Figure 1:
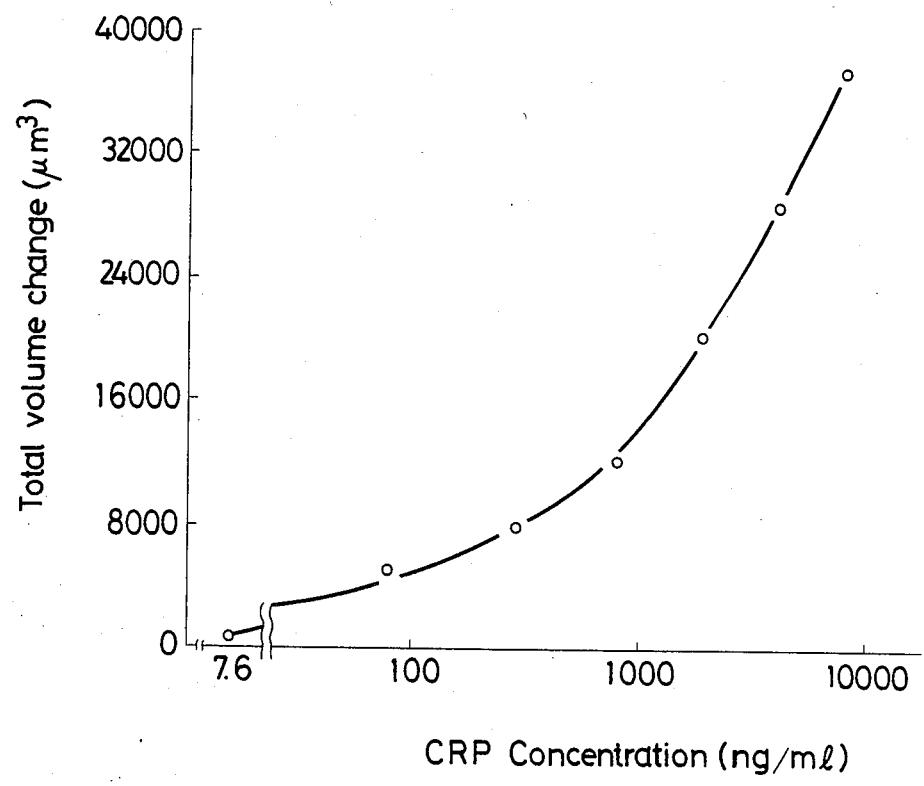

United States Patent [19]

Sakai et al.

[11] Patent Number: 4,680,274

[45] Date of Patent: Jul. 14, 1987

[54] PARTICLES FOR INHIBITING NON-SPECIFIC IMMUNOREACTION

[75] Inventors: Yasuo Sakai; Miyoshi Hirata, both of Tokyo, Japan

[73] Assignee: Daiichi Pure Chemicals Co., Ltd., Tokyo, Japan

[21] Appl. No.: 739,278

[22] Filed: May 30, 1985

[30] Foreign Application Priority Data

Jun. 1, 1984 [JP] Japan .................................. 59-112419

[51] Int. Cl.[4] .................. G01N 33/563; G01N 33/543
[52] U.S. Cl. ...................................... 436/512; 436/518; 436/523; 436/533; 436/825; 436/826; 435/7; 435/23
[58] Field of Search ............... 436/518, 523, 533, 512, 436/825, 826; 435/7, 23

[56] References Cited

U.S. PATENT DOCUMENTS

| 4,020,151 | 4/1977 | Bolz et al. | 436/825 |
| 4,310,508 | 1/1982 | Siber | 436/533 |
| 4,362,531 | 12/1982 | de Steenwinkel et al. | 436/825 |
| 4,569,919 | 2/1986 | Toth et al. | 436/533 |

*Primary Examiner*—Christine M. Nucker
*Assistant Examiner*—Stephen C. Wieder
*Attorney, Agent, or Firm*—Oblon, Fisher, Spivak, McClelland & Maier

[57] ABSTRACT

In an immunoassay, ultrafine particles having an average particle size of 0.2 μm or smaller and sensitized with a substance, which has reactivity with the materials to induce a nonspecific immunoreaction, are added to a sample to inhibit the nonspecific immunoreaction. The above immunoassay can avoid the influence of nonspecific factors more effectively, thereby permitting accurate measuremens on the concentrations of antigens in samples such as blood, urine, body fluid and the like.

11 Claims, 1 Drawing Figure

PARTICLES FOR INHIBITING NON-SPECIFIC IMMUNOREACTION

This invention relates to an immunoassay, and more specifically to an immunoassay of an antigen in a body fluid, in which specific ultrafine particles are used to inhibit a false-positive reaction, which takes place by the materials to induce (hereinafter called "nonspecific factor") a nonspecific immunoreaction, so that the correct quantitative analysis can be made on the antigen in the body fluid.

In recent years, the detection of various factors, proteins, hormones, chemicals and their metabolic products in blood or the measurement of their concentrations has been finding their importance in the determination of conditions and diagnosis of diseases and their treatment methods, their prognostication, etc. As measurement methods of these various substances, there are physiochemical methods, biochemical methods, immunological methods and so on. Of these methods, immunological methods are used widely for the measurement of hormones, chemicals, serum proteins and the like because they permit highly-sensitive, specific and accurate measurements. Usually, each of these immunological methods makes use of an antigen-antibody reaction in which a target substance (hereinafter called "antigen") is reacted with an antibody, which has been obtained by immunizing an animal such as rabbit, goat, guinea pig, sheep, mouse or the like with the target substance, or with a monoclonal antibody obtained by the cell fusion technique. Depending on measurement means and methods, immunological methods include a variety of methods such as single radial immunodiffusion, immunoelectrophoresis, precipitin reaction, agglutination, enzymoimmunoassay, fluoroimmunoassay and radioimmunoassay.

However, measurement results may often be accompanied by errors due to nonspecific reactions which tend to take place in such antigen-antibody reactions, whereby likely to give serious influence to clinical diagnoses. In order to avoid such nonspecific reactions, it has conventionally be adopted such countermeasures as isolation and purification of antigens, absorption of antibodies, or pretreatments of samples. It is however known that samples contain nonspecific factors unremovable by such countermeasures, for example, rheumatoid factor (RF), the first fragment, i.e., q-fragment (Clq) of complement, etc. Of these nonspecific factors, RF is immunoglobulin belonging to the family of immunoglobulin M (IgM) [partly, immunoglobulin G(IgG)] and having a sedimentation coefficient of 19S. It frequently occurs in the bloods of patients who are suffering from autoimmune diseases led by systemic lupus erythematosus (SLE) and chronic rheumatism. Although this RF is believed to be a sort of autoantibodies which react with IgG, it undergoes strong reactions with IgGs of different species as a matter of fact. For these reasons, the existence of RF in a sample gave problems on measurements when one wanted to make correct measurement on the concentration of an antigen in a sample such as blood, urine, body fluid or the like by immunoassay.

As methods for solving the above problems to some extents, it has conventionally been practiced:

(1) to inactivate RF with 2-mercaptoethanol (2-ME), dithiothreitol (DTT) or the like;

(2) to use a non-reactive antibody for RF, such as F(ab')$_2$ fragment obtained by digesting an antibody with an enzyme or the like; and (3) to absorb RF with a denatured antibody obtained by subjecting an immunoglobulin to a heat treatment or with a fragment obtained by digesting the denatured immunoglobulin with an enzyme.

All of these methods were however insufficient from the removal of the influence of RF. In the case of the method (1) for example, it is necessary to use an SH-compound at a high concentration if one wants to inactivate RF with the SH-compound. Moreover, the effectiveness of inactivation by such an SH-compound is also at issue. Namely, the treatment of RF of the IgM type by an SH-compound will exhibit effectiveness if the concentration of the SH-compound is raised. No effects may in many instances be observed for RF of IgG type even if such an SH-compound is used at high concentrations. The method (1) is accompanied by another drawback that if the concentration of the SH-compound is increased further, it will affect even an antibody component itself which will take a part in an antigen-antibody reaction. In the case of the method (2), there is a problem with respect to the non-reactivity of F(ab')$_2$ fragment or the like to RF. It has conventionally be considered that RF reacts primarily with the Fc fragment component out of antibody components but does not react with the F(ab')$_2$ fragment component. As a matter of fact, the existence of RF capable of reacting with the F(ab')$_2$ fragment component has however been known. Even if an antibody rendered free of the $F_c$ fragment by an enzymatic treatment should be used, it will be difficult to get rid of the influence of RF completely. In the case of the method (3), it will be essential to use a denatured antibody or its decomposition product at a high concentration in order to avoid the influence of RF to a certain effective degree. Even if employed at a high concentration, its effectiveness will be insufficient. Moreover, there is another problem on the stability of a reagent which is to be used to avoid the influence of RF.

Furthermore, it has also been practiced for the prevention of influence by a nonspecific factor other than RF, for example, Cl$_q$ or the like to employ such a method as inactivation of each sample (for example, a heat treatment at 56° C. for 30 minutes) or removal of the sample by centrifugation. These methods however require pretreatment of samples and their practice is complex. Therefore, they lack actual utility.

With the foregoing circumstances in view, the present inventors have carried out an extensive research in order to provide a method for avoiding the influence of nonspecific factors more effectively in immunoassays. In the course of the research, an investigation was carried out on the reactivities of certain RF-containing nonspecific factors with immunoglobulin components in various state, for example, with soluble IgG, the F(ab')$_2$ fragments of immunoglobulin which fragments are obtained by digesting the immunoglobulin with an enzyme or the like, denatured IgG obtained by subjecting soluble IgG to heat treatments, solidified immunoglobulin obtained by causing carriers or the like to bear the above immunoglobulin or fragments either singly or as mixtures. The term "solidified" as used herein means that an antibody has been converted into a solid state. As a result, the degrees of their activities were in the order of solubilized F(ab')$_2$ fragments < solubilized immunoglobulin < denatured immunoglobulin < < solidified immunoglobulin. Namely, it has been found that the reactivities of such RF-containing nonspecific factors with solidified immunoglobulin are extremely high. Accordingly, the denatured immunoglobulin which was added for absorption showed lower percent inhibitions against nonspecific agglutinations despite of their higher concentrations than the immunoglobulin immobilized and solidified on the carriers. On the other hand, the percent inhibitions of the solubilized immunoglobulin and solubilized F(ab')$_2$ fragments were also at low levels compared with denatured immunoglobulin. However, the solidified immunoglobulin obtained by causing, especially, ultramicrosphere suspension to bear these solubilized immunoglobulin or denatured immunoglobulin or their digesting products are more reactive with such nonspecific factors than any of the remaining antibody components. More surprisingly, it has also been found that those obtained by causing ultrafine particulate carriers to bear high molecular substances having stabilizing effects as protective colloids have reactivities with such nonspecific factors, which reactivities are substantially equal to or higher than the reactivities of the above-described solidified antibodies. The present invention has been completed as a result of an extensive research which has been conducted paying attention to the above-mentioned fact, namely, to apply ultrafine particles sensitized a substance which has reactivity with a nonspecific factor in a sample, to immunoassay.

Accordingly, the present invention provides an immunoassay in which ultrafine particles (hereinafter called "ultramicrosphere suspension") carrying a substance having reactivity with a nonspecific factor (hereinafter called "nonspecific-factor absorbing substance") and having an average particle size of 0.2 $\mu$m or smaller are added to a sample to inhibit a nonspecific immunoreaction.

The immunoassay of this invention can avoid the influence of nonspecific factors more effectively, thereby permitting accurate measurements on the concentrations of antigens in samples such as blood, urine, body fluid and the like.

The above and other objects, features and advantages of the present invention will become apparent from the following description and the appended claims, taken in conjunction with the accompanying drawing, in which:

FIG. 1 is a calibration curve obtained in accordance with the electrical resistance method, in which total volume changes are plotted against CRP concentrations.

Ultramicrosphere suspension useful in the practice of this invention have an average particle size of 0.2 $\mu$m or smaller. It is however preferred to use ultramicrospheres the average particle size of which ranges from about 0.01 $\mu$m to 0.1 $\mu$m. As materials making up such ultramicrosphere suspension, may for example be mentioned inactivated virus, synthetic resins such as artificial or chemically-synthesized polyamides, polyvinylidene chlorides, polyvinyl chlorides, acrylic resins, polyvinyl acetates, polystyrenes, polypropylenes, polyepoxy resins, urethanes, polyethylenes and the like, and inorganic materials such as activated carbon, carbon black, kaolin, bentonite, zeolite, alumina and the like. There is no particular limitation imposed on the shapes of such ultramicrospheres. Therefore, they may for example be spherical or polygonal. They may also be porous. In the present invention, the smaller the particle sizes of ultramicrospheres, the better. It is therefore rational to replace the above-mentioned ultramicrospheres by ultramicrospheres having an average particle size smaller than 0.01 $\mu$m if the latter ultramicrospheres become available in the future. Any average particle sizes greater than 0.2 $\mu$m are however not preferred because they lead to increased volumes of fine particles, whereby disturbing measurements.

As nonspecific-factor absorbing substances useful in the practice of this invention, may for example be mentioned substances having stabilizing effects as protective colloids, or normal immunoglobulin components of animal or human derivation or substances obtained by subjecting such normal immunoglobulin components to enzymatic treatments or physical or chemical treatments. As substances having stabilizing effects as protective colloids, may for example be mentioned hydrophilic high-molecular substances such as serum albumin, hydrophilic high-molecular polymers, etc. On the other hand, as normal immunoglobulin components of animal or human derivation, may for example be mentioned $\gamma$-globulin, the IgG fragment obtained by purifying $\gamma$-globulin in accordance with column chromatography, etc. As substances obtained by subjecting normal antibody components to enzymatic treatments, may for example be mentioned a variety of fragments obtained by treating such normal immunoglobulin components with proteolytic enzymes. These nonspecific-factor absorbing substances are then carried by ultramicrospheres by usual methods, namely, by causing them to bear such absorbing substances either singly or as mixtures by physical adsorption or chemical covalent bonding. Although no particular limitation is imposed on the amount of each nonspecific-factor absorbing substance to be employed for its immobilization, it is preferred to choose a suitable amount depending on the amount of a target substance in a sample, the particle size of ultramicrospheres, the amount of the ultramicrospheres, etc.

The measurement technique of this invention may be applied to substantially all conventional immunoassays, for example, agglutination, agglutination-inhibitory reaction, immunonephelometry, enzymoimmunoassay, fluoroimmunoassay, radioimmunoassay, laser nephelometry, and so on.

A description will next be made taking, by way of example, the technique of this invention applied to agglutination, enzymoimmunoassay, fluoroimmunoassay, radioimmunoassay, laser nephelometry and the like.

(1) Agglutination:

A suspension is prepared by mixing fine particles, obtained by causing a fine particulate carrier such as hemocytes, kaolin, bentonite, polystyrene latex or the like to carry an antigen or antibody by physical adsorption or chemical covalent bonding, with ultramicrospheres of this invention. Upon addition of this suspension to a sample, the antigen- or antibody-bearing fine particles are caused to undergo agglutination on the basis of an antigen-antibody reaction. This agglutination product or the unreacted sensitized fine particles are detected by the latex agglutination test in which the agglutination pattern is visually determined, immunonephelometry in which a change in optical absorbancy is determined, laser nephelometry the principle of which depends on optical scattering, or electrical resistance method (Coulter principle) or laser scattering method in which a volume or other numerical change of the agglutination product or the unreacted antigen- or antibody-bearing fine particles is detected.

Certain aspects, in principle, of the technique of this invention applied by way of example to agglutination will next be described. Although the average particle size of antigen- or antibody-bearing fine particles, which are employed usually, ranges from 0.2 to several micrometers, especially, from 0.3 to 2.0 micrometers, the average particle size of ultramicrospheres pertaining to the present invention is 0.2 μm or smaller. Accordingly, the volume of the ultramicrospheres is extremely small compared with the volume of antigen- or antibody-bearing fine particles useful for an antigen-antibody reaction (the volume ratio may for example be 1:8000 where the particle size of ultramicrospheres is 0.05 μm and that of fine particles for the antigen-antibody reaction is 1.0 μm). Even if the ultramicrospheres have undergone agglutination by a nonspecific factor and their volume has increased by several tens to 100 times, the thus-increased volume is still far smaller compared with the volume of the antigen- or antibody-bearing fine particles. Therefore, the nonspecific agglutination product of the ultramicrospheres does not give any influence to the measurement system in an immunoassay which relies upon the detection of a change due to an antigen-specific forward reaction in which fine antigen- or antibody-bearing particles take a part, for example, (1) the immunoassay for visually detecting changes in agglutination pattern by the latex agglutination test, (2) the immunoassay for detecting volume or other numerical changes by the electrical resistance method or laser scattering method, or (3) the immunoassay for detecting changes in optical scattering by the laser nephelometry. It is also possible to avoid the influence of such a nonspecific agglutination product in the immunonephelometry (4) in which an antigen-antibody reaction is optically detected, provided that suitable selections are made on the particle size of ultramicrospheres and the measurement wavelength. As mentioned above, use of ultramicrospheres permits the removal of influence of nonspecific factors such as RF in an immunoassay, which is adapted to detect a specific antigen-antibody reaction product, without affecting the measurement system.

As fine particles useful for the immobilization of an antigen or antibody in agglutination, it is possible to use any fine particles which have been used to date, including for example particles derived from living bodies, such as bacteria and erythrocytes; particles not derived from living bodies, such as silica, carbon black, kaolin, bentonite, glass beads, agarose and alumina; artificially and chemically synthesized, synthetic high molecular particles such as polyamide particles, polyvinylidene chloride particles, polyvinyl chloride particles, acrylic resin particles, polyvinyl acetate particles, polystyrene particles, polypropylene particles, polyepoxy resin particles, urethane particles and polyethylene particles; etc.

(2) Enzymoimmunoassay, fluoroimmunoassay and radioimmunoassay:

(i) Sandwich method: When a solid phase, with a specific antibody conjugated therewith, and ultramicrospheres of this invention are reacted with a sample containing an unknown amount of a target antigen, an antigen-antibody complex is formed by an antigen-antibody reaction (primary reaction). Upon further reaction with a prescribed amount of a labelled antibody, the labelled antibody is allowed to conjugate with the complex (secondary reaction). However, the ultramicrospheres and unreacted labelled antibody still remain in free state in the liquid phase. Thereafter, the solid phase and liquid phase are separated from each other. The unknown amount of the antigen is then determined by measuring the activity of the labelling agent in the solid or liquid phase and quantitatively analyzing the unknown amount of the antigen in accordance with a standard curve which has been prepared separately by using standard solutions of known concentrations.

(ii) Competitive method: When an unknown amount of a target antigen and a prescribed amount of a labelled antigen are competitively reacted with an antibody conjugated with a solid phase in the presence of ultramicrospheres pertaining to the present invention, the ultramicrospheres are allowed to remain floating in the liquid phase while the target antigen and labelled antigen are allowed to conjugate, in amounts proportional to their concentrations, with the antibody in the solid phase. Namely, the amount of the labelled antigen to be conjugated with the antibody will increase or decrease in inverse proportion with the amount of the target antigen contained in the sample. Thereafter, the solid phase and liquid phase are separated from each other, the activity of the labelling agent in the solid or liquid phase is measured, and the unknown amount of the antigen is quantitatively analyzed from a standard curve prepared separately.

(iii) Second antibody method: When a sample containing an unknown amount of a target antigen is mixed with corresponding antibody and labelled antigen to effect an antigen-antibody reaction in the presence of ultrafine absorbent particles pertaining to the present invention, the target antigen and labelled antigen are allowed to react, in amounts proportional to their respective concentrations, with the antibody (primary reaction). Then, an antibody (second antibody) to the above antibody is added to induce agglutination (secondary reaction) with the immune complex formed by the primary reaction. In some instances, the second antibody may be added simultaneously upon conducting the primary reaction. The agglutination products formed by the secondary reaction are thereafter separated by centrifugation, followed by its washing. Since the ultrafine particles and the agglutination product formed from the ultramicrospheres and the nonspecific factor do not precipitate by centrifugation at the usual revolution speed of 5000 rpm or less, the labelled antigen reacted with the antibody is concentrated in the precipitate fraction while the ultramicrospheres and unreacted labelled antigen are both concentrated in the supernatant fraction. The activity of the labelling agent in the precipitate or supernatant fraction is measured, and the unknown amount of the antigen is then quantitatively analyzed from a standard curve which has been prepared separately.

As materials of insoluble solid-phase carriers useful for solidifying the antigen or antibody in the method (i) or (ii), any materials may be used so long as they have been used in conventional immunoassays, including for example polystyrene, polyethylene, polyacrylic resins, TEFLON, nylons, polyacetals, paper, glass, agarose, etc. Their shapes may be spherical, rod-like or plate-like. For example, they may be used in the form of containers such as testing tubes, optical cells or the like.

As labelling agents useful for the labelling of the antigen or antibody in the method (i), (ii) or (iii), it is possible to use enzymes, fluorescent substances, isotope-containing compounds and the like. Here, use of an enzyme leads to an enzymoimmunoassay, use of a fluorescent substance results in a fluoroimmunoassay, and use of an isotope leads to a radioimmunoassay.

As exemplary antibodies useful in the above method (1) or (2), may be mentioned antiserums obtained by immunizing animals such as rabbits, goats, guinea pigs, sheep, mice and the like with antigens, γ-globulins obtained by purifying such antiserums, IgG fragments obtained by isolating the γ-globulins by column chromatography, various fragments obtained by digesting the IgG fragments by proteolytic enzymes such as papain and pepsin. They may be used either singly or in the forms of mixtures.

This invention will hereinafter be described by the following Examples.

EXAMPLE 1

(1) Preparation of ultramicrosphere suspension:

(i) Mixed promptly were 0.34 ml of a 10% latex suspension having a particle size of 0.085 μm (product of Dow Chemical Company) and 3.0 ml of 0.5% bovine serum albumin (hereinafter abbreviated as "BSA"). The resultant mixture was allowed to stand at room temperature for 2 hours. Thereafter, the mixture was subjected to ultracentrifugation at 25,000 rpm to wash and remove unimmobilized BSA. The residue was suspended again in a 0.05 M glycine buffer (pH 9.0) which contained 0.1% of $NaN_3$ and 0.2% of BSA. The resultant suspension was filtered through a membrane filter, and the filtrate was stored at 4° C.

(ii) Mixed promptly were 0.5 ml of a 10% latex suspension having a particle size of 0.109 μm (product of Dow Chemical Company) and 4.5 ml of 0.5% BSA. The resultant mixture was allowed to stand at room temperature for 2 hours. Thereafter, the mixture was subjected to ultracentrifugation at 20,000 rpm to wash and remove unimmobilized BSA. The residue was suspended again in a 0.05 M glycine buffer (pH 9.0) which contained 0.1% of $NaN_3$ and 0.2% of BSA. The suspension was stored at 4° C.

(iii) Mixed promptly were 0.5 ml of a 10% latex suspension having a particle size of 0.254 μm (product of Japan Synthetic Rubber Co., Ltd.) and 4.5 ml of 0.5% BSA. The resultant mixture was allowed to stand at room temperature for 2 hours. Thereafter, the mixture was subjected to ultracentrifugation at 20,000 rpm to wash and remove unimmobilized BSA. The residue was suspended again in a 0.05 M glycine buffer (pH 9.0) which contained 0.1% of $NaN_3$ and 0.2% of BSA.

(2) Preparation of latex suspension sensitized with anti-CRP antibody:

A 10% latex suspension having a particle size of 0.804 μm (product of Dow Chemical Company) was diluted 10 times with a 0.05 M glycine buffer (pH 8.5), to which 0.5–2.0 mg/ml (which was changed in accordance with the potency of the used antibody) of the IgG fragment of the rabbit anti-CRP antibody was added in an equal amount. The resultant mixture was allowed to stand at room temperature for 30 minutes. Then, the same buffer which contained 0.5% of BSA was added and mixed in the same amount. After allowing the thus-obtained mixture to stand for additional 1–2 hours, the unsensitized IgG was washed and removed by centrifugation and the residue was suspended again in the same buffer which contained 0.2 % of BSA and 0.1% of $NaN_3$. The suspension was stored at 4° C.

(3) Measurement of CRP by the latex agglutination test:

Agglutination was conducted by dropping, onto glass plates, 30 μl portions of various samples such as normal human serum, standard solution of CRP and serum pooled from patients and those prepared by adding purified RF [purified in accordance with the procedure described in "Immunology", 15, 549(1968)] to portions of these samples, together with 30 μl portions of a latex bearing the anti-CRP antibody, alone, and mixed suspensions obtained respectively by mixing the latex with the ultramicrosphere suspension which had been obtained in the above procedures (i), (ii) and (iii). Results judged in accordance with the following judgement standard are summarized in Table 1.

Judgement standard:

+ + +: Extremely positive

+ +: Very positive

+: Positive

±: Doubtful positive

−: Negative

As shown in Table 1, agglutination images were "+ + +" in the groups added with RF (b and d) irrespective of the presence or absence of CRP or its amount when the latex suspension bearing the anti-CRP antibody was used singly. Thus, false-positive reactions took place apparently. This phenomenon was also observed when RF was added to the CRP-negative patient serum (e - ii). When the subject mixed suspension of the ultramicrospheres having a particle diameter of 0.085 μm or 0.109 μm and the latex bearing the anti-CRP antibody was employed, agglutination was however observed only on the samples (c, d, e - iii, iv) which were positive with respect to CRP, i.e., the target antigen. Even when applied to the samples (b, e - ii) which were CRP-negative but RF-positive, no nonspecific agglutination due to false-positive reaction was observed. On the other hand, when the mixed suspension of the ultramicrospheres having a particle size of 0.254 μm, which is beyond the upper limit of the particle size range defined in the present invention, and the latex bearing the anti-CRP antibody was employed, the false-positive reaction due to the nonspecific immunoreaction caused by RF was not suppressed to any significant extent.

TABLE 1

| Type of sample | Latex bearing anti-CRP antibody, alone | Latex bearing anti-CRP antibody + ultramicrosphere suspension (μm) | | |
|---|---|---|---|---|
| | | 0.085 | 0.109 | 0.254 |
| a. Normal human serum | − | − | − | − |
| b. RF-added normal human serum | + + + | − | − | ± |
| c. Standard CRP solution (RF-negative) | | | | |
| 0.01 μg/ml | ± | ± | ± | ± |
| 0.1 | + | + | + | + |
| 1.0 | + + | + + | + + | + + |
| d. Standard CRP solution (RF-added) | | | | |
| 0.01 μg/ml | + + + | ± | ± | + + |

TABLE 1-continued

| Type of sample | Latex bearing anti-CRP antibody, alone | Latex bearing anti-CRP antibody + ultramicrosphere suspension (μm) | | |
|---|---|---|---|---|
| | | 0.085 | 0.109 | 0.254 |
| 0.1 | +++ | + | + | ++ |
| 1.0 | +++ | ++ | ++ | +++ |
| e. Patient serum | | | | |
| (i) CRP(negative),RF(negative) | − | − | − | − |
| (ii) CRP(negative),RF(positive) | +++ | − | − | ++ |
| (iii) CRP(positive),RF(negative) | ++ | ++ | ++ | ++ |
| (iv) CRP(positive),RF(positive) | +++ | +++ | +++ | +++ |

EXAMPLE 2

(1) Preparation of ultramicrosphere suspension:

Mixed promptly were 5.0 ml of a 10% latex suspension having a particle size of 0.07 μm (product of Rhône Poulanc SA) and 5.0 ml of 0.1% F(ab')$_2$ fragment of normal immunoglobulin. The resultant mixture was allowed to stand at room temperature for 1 hour. Thereafter, the mixture was subjected to gel filtration chromatography on a Sepharose 6B column which had been equilibrated with a 0.05 M glycine buffer (pH 9.0) with 0.1% of NaN$_3$ and 0.2% of BSA contained therein, whereby to remove the unimmobilized normal immunoglobulin. After adjusting the final concentration to 1.0%, the filtrate was stored at 4° C.

(2) Preparation of latex suspension bearing anti-AFP monoclonal antibodies:

Mixed promptly were a 1% latex suspension having a particle size of 0.804 μm (product of Dow Chemical Company) (in 0.05 M glycine buffer, pH 8.5) and 5 ml of 0.5 mg/ml IgG fragment (a mixture of three kinds of clones) of the anti-AFP monoclonal antibodies. The resultant mixture was allowed to stand at room temperature for 2 hours. Then, 5 ml of the same buffer which contained 0.5% of BSA was added. After washing and removing the unimmobilized IgG by centrifugation, the residue was added to the same buffer, which contained 0.2 % of BSA and 0.1% of NaN$_3$, so that the residue was suspended again. The suspension was stored at 4° C.

(3) Mixing of ultramicrosphere suspension with particles bearing anti-AFP monoclonal antibodies:

The ultramirosphere suspension obtained in the above procedure (1) and the latex suspension described in the above procedure (2) bearing the anti-AFP monoclonal antibodies were mixed in such amounts that their final concentrations reached 1.0% and 0.2% respectively, thereby providing an AFP-measuring reagent (B). As a control, a suspension containing, as a sole component, latex particles bearing the anti-AFP monoclonal antibodies without addition of any ultramicrosphere suspension thereto was employed as an AFP-measuring reagent (A).

(4) Measurement of AFP by Coulter principle:

Mixed respectively were 50 μl portions of various samples with 50 μl portions of the AFP-measuring reagents (A) and (B), followed by their reactions at 37° C. for 10 minutes. After diluting the reaction mixtures 100-500 times respectively, the agglutination products obtained respectively by the reactions were measured in terms of volume changes by the electrical resistance method (Coulter principle) which employed a Coulter counter ZBI & C - 1000.

As the samples, were employed the standard AFP solution, patient sera, and those obtained by adding purified RF to portions of the standard AFP solution and patient sera. Results are summarized in Table 2.

TABLE 2

| | Volume change of agglutination product | |
|---|---|---|
| Type of sample | AFP-measuring reagent (A) | AFP-measuring reagent (B) |
| a. Standard AFP solution (RF-non-added) | | |
| 7 ng/ml | 363 | 372 |
| 76 | 7207 | 7312 |
| 760 | 11956 | 12004 |
| 7600 | 32280 | 32413 |
| b. Standard AFP solution (RF-added) | | |
| 7 ng/ml | 36540 | 380 |
| 76 | 37666 | 7352 |
| 760 | 39228 | 12106 |
| c. Patient sera | | |
| (i) AFP-negative | 22 | 6 |
| (ii) AFP-negative, RF-positive | 16988 | 13 |
| (iii) AFP-negative + RF-added | 37019 | 10 |
| (iv) AFP-positive | 8623 | 8640 |
| (v) AFP-positive, RF-positive | 27226 | 8620 |
| (vi) AFP-positive + RF-added | 38566 | 615 |

As shown in Table 2, the volumes of the agglutination products increased similarly in accordance with the concentrations of the angigen (AFP) irrespective whether the AFP-measuring reagent (A) or (B) was used, when the sample was the standard AFP solution (a) added with no RF. It is thus possible to quantitatively analyze the AFP concentration of each unknown sample on the basis of a calibration curve obtained by plotting the volumes of agglutination products along the axis of ordinates and AFP concentrations along the axis of abscissas (see, FIG. 1). In the case of the sample (b) with RF contained therein, the AFP-measuring reagent (A) was unable to make correct measurements because false-positive reactions, which were not dependent on the AFP concentration and were caused by antigen-nonspecific RF or the like, took place. Unlike the AFP-measuring reagent (A), no RF-induced non-specific false-positive reactions were observed with the AFP-measuring reagent (B) even if RF was contained in samples. These facts were also observed with the various patient sera. Especially in the case of the AFP-negative and RF-positive group (c - ii), false-positive reactions were strongly observed with the AFP-measuring reagent (A) although AFP was not contained in the sample. These false-positive reactions became more remarkable in the case of the group (c - iii) which was obtained by incorporating more purified RF to the group (c - ii). On the other hand, no RF-induced nonspecific false-positive reactions were observed with the AFP-measuring reagent (B) even when RF was present. It was thus possible to conduct specific and correct measurements on AFP (c - ii, iii, v and vi). The above facts were also observed when latex particles bearing the F(ab')$_2$ fragment of the anti-AFP monoclonal antibodies, which had been obtained by using the F(ab')$_2$ fragment of the anti-AFP monoclonal antibody as an antibody to be employed for its immobilization, were used as an AFP-measuring reagent.

EXAMPLE 3

(1) Preparation of normal immumoglobulin and its processed products:

(a) Solubilized normal IgG: A non-adsorbed fragment obtained from normal goat serum in a usual manner, more specifically, the normal goat IgG obtained by dialyzing a 35% ammonium sulfate fraction of normal goat serum against a 0.05 M phosphate buffer (pH 8.0), adding the resultant dialysate to a DEAE-Sephacel column which had been equilibrated against the buffer, and then eluting the column with the same buffer was used as a solubilized normal antibody.

(b) Solubilized F(ab')$_2$ fragment: After enzymatically digesting the IgG fragment obtained in the procedure (a) with pepsin, the digested material (F(ab')$_2$) was purified by column chromatography making use of DEAE-Sephacel or CM-sepharose.

(c) Denatured antibody: Thermally-denatured IgG, which had been obtained by subjecting the IgG fragment obtained in the above procedure (a) to a heat treatment at 63° C. and for 10 minutes, was used as a denatured antibody.

(2) Preparation of ultramicrosphere suspension:

(a) Stabilized ultramicrosphere suspension: Promptly mixed were 0.5 ml of a 0.5% latex suspension having a particle size of 0.085 μm (product of Dow Chemical Company) and 4.5 ml of 0.2% BSA. Subsequent operations were conducted in accordance with the procedure (1) of Example 1.

(b) Solidified antibody: Promptly mixed were 5.0 ml of a 0.5% latex suspension having a particle size of 0.085 μm (product of Dow Chemical Company) and 5.0 ml of the normal immunoglobulin (IgG) obtained in the above procedure (1)-a). Subsequent operations were conducted in accordance with the procedure (1) of Example 2.

(3) Latex particles bearing normal immunoglobulin:

They were obtained by causing latex particles of 0.804 μm (product of Dow Chemical Company) to sensitize the IgG fragment, which had been derived from normal rabbit serum, following the procedure (2) of Example 1.

(4) Study on the reactivities between normal immunoglobulin components or their processed products and RF:

Differences among the reactivities of the various immunoglobulin components obtained by the above-mentioned procedure (1) with RF were studied by investigating how much the reaction between the fine particles bearing the IgG fragment of normal antibody, which particles had been obtained in the above procedure (3), and RF would be hindered by the various immunoglobulin components or the ultramicrosphere suspension obtained by the above-mentioned procedure (2), in other words, using the absorptions of RF activity by these immunoglobulin components as indexes (see, Table 3). The measurements were effected in the same manner as in Example 1, namely, by determining volume changes in accordance with the electric resistance method (Coulter principle). Their differences in reactivity with RF are expressed in terms of the percentages of changes of their corresponding agglutination products and the percentages of absorbed RF determined from the percentages of changes. Results are shown in Table 3.

TABLE 3

| Various antibody components | Volume change of agglutination product (%) | Absorption of IgG (%) |
|---|---|---|
| None | 100 | — |
| Solubilized F(ab')$_2$ fragment (10 mg/ml) | 97.6 | 2.4 |
| Solubilized IgG (10 mg/ml) | 94.4 | 5.6 |
| Denatured IgG (10 mg/ml) | 19.0 | 81.0 |
| (1 mg/ml) | 46.8 | 53.2 |
| [Ultramicrosphere suspension] | | |
| Solidified IgG (0.8 mg/ml) | 0.5 | 99.5 |
| BSA (5 mg/ml) | 0.2 | 99.8 |

As a result, the RF-absorbing effects of the ultramicrosphere suspension were more significant than those of any immunoglobulin components in the various other state as shown in Table 3. Especially, the amount of the antibody which took a part as the solidified antibody in the reaction with RF was 0.8 mg which was smaller than the amount (10 mg/ml) of any other antibody component (i.e., less than one tenth). Nevertheless, the solidified antibody showed the high percentage of absorbed RF. It was therefore demonstrated that the solidified antibody had superior reactivity with RF.

EXAMPLE 4

(1) Preparation of ultramicrosphere suspension:

After promptly mixing 0.5 ml of a 10% latex suspension having a particle size of 0.07 μm (product of Rhône Poulanc SA) and 4.5 ml of 0.1% normal goat immunoglobulin, the resultant mixture was allowed to stand at room temperature for 1 hour. Thereafter, 2.5 ml of a 0.05 M glycine buffer (pH 9.0) which contained 0.5% of BSA was added further. The thus-obtained mixture was allowed to stand for further 2 hours. Then, it was centrifuged at 22,000 rpm to wash and remove the unimmobilized immunoglobulin. The residue was then suspended again in a 0.05 M phosphate buffer (pH 7.2) which contained 0.02% of NaN$_3$ and 0.2% of BSA.

(2) Preparation of anti-FDP monoclonal antibody-enzyme conjugate:

After coupling 0.5 ml of the Fab' fragment of the 0.5 mg/ml anti-monoclonal antibody and 1.0 mg of 2 mg/ml β-D-galactosidase by using o-nitrophenylenediamine as a crosslinking agent, the resultant reaction mixture was subjected to column chromatography through Sephadex G-200 to remove the unreacted enzyme and antibody, thereby purifying the enzyme-antibody conjugate.

(3) Preparation of FDP-immobilized polystyrene beads:

Polystyrene beads (diameter: 6 mm) were added to a 0.1 M sodium carbonate buffer (pH 9.0) containing 2 μg/ml FDP dissolved therein. The resultant mixture was allowed to stand at 4° C. for 24 hours. Thereafter, the unimmobilized FDP was washed and removed by the same buffer which contained 2% of BSA. The resultant FDP-immobilized polystyrene beads were stored at 4° C. while allowing them to float in the same buffer.

(4) Enzymoimmunoassay of FDP:

After reacting the ultramicrosphere suspension obtained in the above procedure (1), RF-positive or RF-negative sample diluted with a phosphate buffer, or the standard FDP solution with the enzyme-antibody conjugate obtained in the above procedure (2) at room temperature for 20 minutes, the FDP-immobilized beads obtained in the above procedure (3) were added to the reaction mixture and then reacted for further 20 minutes. The beads were washed with the same buffer and were then placed in a test tube which was provided on the side. A substrate solution (10 mM o-nitrophenyl-β-D-galactopyranoside) was added to the test tube. After reacting the resultant mixture at 37° C. for 15 minutes, a 0.1 M sodium carbonate solution was added to terminate the enzymatic reaction. The absorbancy of the reaction mixture was measured at 420 nm. Based on absorbancies obtained in this manner, the FDP concentrations in the various samples were determined with reference to a standard curve which had been obtained by plotting absorbancies obtained by processing the standard FDP solution in the same manner as that described above along the axis of ordinates and FDP concentrations along the axis of abscissas.

TABLE 4

| Various samples (name) | FDP concentration (μg/ml) | |
|---|---|---|
| | System diluted by buffer | System diluted by ultrafine absorbent particles |
| a. RF-negative, FDP-negative | | |
| Y.S. | 0.2 | 0.2 |
| Y.K. | 0.1 | 0.0 |
| b. RF-negative, FDP-positive | | |
| K.K. | 3.5 | 3.6 |
| H.S. | 2.6 | 2.4 |
| c. RF-positive, FDP-negative | | |
| T.N. | 4.4 | 0.1 |
| Y.Y. | 3.2 | 0.0 |
| K.U. | 2.1 | 0.2 |
| d. RF-postive, FDP-positive | | |
| S.S. | 5.8 | 2.3 |
| M.A. | 4.9 | 1.7 |
| K.H. | 7.2 | 3.3 |

With the systems in which enzymoimmunoassay was conducted by diluting their corresponding samples with the ultramicrosphere suspension, measurement data were obtained at such levels as being dependent on the FDP in the samples in all the groups (the groups a, b, c and d ) as shown in Table 4. Different from such systems, measurement data were obtained at such levels as being independent on the contents of FDP in the case of the systems in which enzymoimmunoassay was conducted after dilution with a phosphate buffer. In other words, in the case of the samples in which RF was negative (groups a and b), data similar to those obtained with the system diluted by the ultramicrosphere suspension were obtained. However, in the case of the samples in which RF was positive, data reflecting false-positive reactions were obtained despite of negative FDP (group c) or higher data were resulted although FDP was positive (group d).

We claim:

1. In an immunoassay for a target antigen in a sample also containing materials capable of inducing non-specific immunoreaction in the immunoassay, wherein a specific immunoreaction proceeds between the target antigen and the corresponding antibody, the improvement which comprises adding to said sample ultrafine particles having an average particle size of 0.2 microns or smaller, which particles contain a substance not participating in said immunoreaction but being capable of inducing reactions with said materials in the sample and absorbing said materials into said particles, to thereby inhibit non-specific immunoreactions between said materials and the corresponding antibody.

2. The immunoassay according to claim 1, wherein the ultrafine particles have an average particle size of about 0.01–0.1 μm.

3. The immunoassay according to claim 1, wherein the substance which is capable of reacting with the materials is a substance having stabilizing effects as a protective colloid.

4. The immunoassay according to claim 3, wherein the substance having stabilizing effects as the protective colloid is serum albumin.

5. The immunoassay according to claim 1, wherein the substance which is capable of reacting with the materials is a normal immunoglobulin component of animal or human derivation or a substance obtained by subjecting the normal immunoglobulin component to an enzymatic treatment or a physical or chemical treatment.

6. The immunoassay according to claim 5, wherein the normal immunoglobulin component is the IgG fragment derived from normal serum.

7. The immunoassay according to claim 5, wherein the substance obtained by subjecting the normal immunoglobulin component to the enzymatic treatment is the F(ab')$_2$ fragment of normal immunoglobulin.

8. The immunoassay according to claim 1, wherein said ultrafine particles are comprised of a material selected from the group consisting of inactivated virus, synthetic resins and inorganic materials.

9. The immunoassay according to claim 8, wherein said synthetic resin is a resin selected from the group consisting of polyamides, polyvinylidene chlorides, polyvinyl chlorides, acrylic resins, polyvinyl acetates, polystrenes, polypropylenes, polyepoxy resins, urethanes and polyethylenes.

10. The immunoassay according to claim 8, wherein said inorgainic material is selected from the group consisting of activated carbon, carbon black, kaolin, bentonite, zeolite, and alumina.

11. The immunoassay according to claim 5, wherein said normal immunoglobulin component is subjected to proteolytic enzyme.

* * * * *